United States Patent [19]

Baker et al.

[11] Patent Number: 4,968,711
[45] Date of Patent: Nov. 6, 1990

[54] TETRAZOLE COMPOUNDS AND USE AS ANTI-ALLERGICS

[75] Inventors: Stephen R. Baker, Yateley; John Goldsworthy, Kempshott Rise; William J. Ross, Lightwater, all of England

[73] Assignee: Lilly Industries Limited, Basingstoke, England

[21] Appl. No.: 182,648

[22] Filed: Apr. 18, 1988

[30] Foreign Application Priority Data

Apr. 22, 1987 [GB] United Kingdom ................ 8709547

[51] Int. Cl.$^5$ .................... C07D 257/04; A61K 31/41
[52] U.S. Cl. .................................... 514/381; 548/252; 548/253
[58] Field of Search .................. 548/252, 253; 514/381

[56] References Cited

U.S. PATENT DOCUMENTS

| 3,600,437 | 8/1971 | Marshall | 548/253 X |
| 4,513,005 | 4/1985 | Baker et al. | 514/451 |
| 4,665,189 | 5/1987 | Baker et al. | 548/252 |
| 4,675,335 | 6/1987 | Baker et al. | 514/381 |

FOREIGN PATENT DOCUMENTS

| 123543 | 10/1984 | European Pat. Off. |
| 228045 | 7/1987 | European Pat. Off. |
| 2144422 | 3/1985 | United Kingdom. |
| 2168704 | 6/1986 | United Kingdom. |
| 2170204 | 7/1986 | United Kingdom. |

OTHER PUBLICATIONS

Bachanan et al. J.OC 12 1969 pp. 1001-1003.

Primary Examiner—David B. Springer
Attorney, Agent, or Firm—Robert A. Conrad; Leroy Whitaker

[57] ABSTRACT

There is disclosed a pharmaceutical compound of the formula

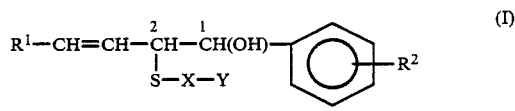

in which $R^1$ is $C_{7-20}$ alkyl, $C_{7-20}$ alkenyl, or $C_{7-20}$ alkynyl, the alkyl, alkenyl or alkynyl group being optionally substituted by phenyl or substituted phenyl, $R^2$ is —CN, —COOR$^3$ or

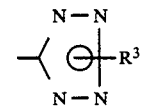

wherein $R^3$ is hydrogen or a protecting group, X is alkylene containing 1 to 6 carbon atoms and Y is a nitrogen-containing group selected from

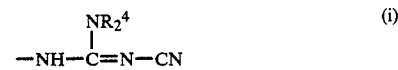

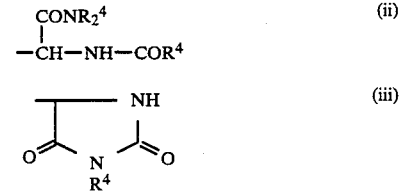

where each $R^4$ independently is hydrogen or $C_{1-4}$ alkyl; and salts thereof.

8 Claims, No Drawings

TETRAZOLE COMPOUNDS AND USE AS ANTI-ALLERGICS

This invention relates to organic compounds and their use as pharmaceuticals.

European Patent Application No. 84305203 (Publication No. 0 134 111) discloses certain compounds of the general formula

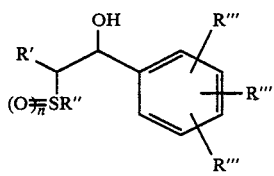

in which n is 0, 1 or 2, R' is an optionally substituted hydrocarbyl group, R" is an optionally substituted phenyl or $C_{1-10}$ alkyl group, and the R''' groups can take various values. The compounds have an antagonist effect on leukotriene receptors.

We have now discovered a small group of related compounds with exceptional properties and activity.

The compounds of the invention are of the following general formula:

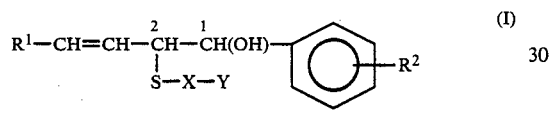

in which $R^1$ is $C_{7-20}$ alkyl, $C_{7-20}$ alkenyl or $C_{7-20}$ alkynyl, the alkyl, alkenyl or alkynyl group being optionally substituted by phenyl or substituted phenyl, $R^2$ is —CN, —COOR$^3$ or

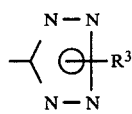

where $R^3$ is hydrogen or a protecting group, X is alkylene containing 1 to 6 carbon atoms and Y is a nitrogen-containing group selected from $$-NH-\underset{\underset{NR_2^4}{|}}{C}=N-CN \quad (i)$$

$$-CH-NH-COR^4 \quad (ii)$$
$$\underset{|}{CONR_2^4}$$

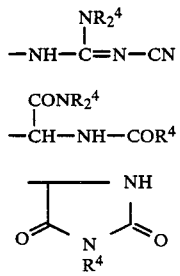 (iii)

where each $R^4$ independently is hydrogen or $C_{1-4}$ alkyl; and salts thereof.

The compounds of the invention, in unprotected form, have been shown to be pharmacologically active in tests which demonstrate their antagonist effect on leukotriene receptors, and indicate their use in the treatment of allergic and other disorders.

In the above general formula when $R^1$ is alkyl it can be branched or unbranched and preferably contains from 8 to 13 carbon atoms. Similarly, when $R^1$ is alkenyl it can be branched or unbranched and preferably contains 8 to 13 carbon atoms. Alkenyl and alkynyl groups preferably contain 1 to 3 unsaturated bonds. When $R^1$ is substituted by phenyl, the phenyl group is preferably attached to the terminal carbon atom. The phenyl group is preferably unsubstituted but it can also be substituted by one or more, such as 1 to 3, substituents selected from, for example, $C_{1-4}$ alkyl, especially methyl, $C_{1-4}$ alkoxy, especially methoxy and ethoxy, hydroxy, nitro, cyano, halo, especially chloro, trifluoromethyl, carboxyl, tetrazolyl and —CONH$_2$.

The group $R^1$ is preferably alkenyl and preferred values of $R^1$ are of the formula $R^5CH=CH-$ where $R^5$ is $C_{7-11}$ alkyl, especially $C_{8-10}$ alkyl, or $CH_3(CH_2)_nCH=CH-CH_2-CH=CH-CH=CH-$ where n is 0 to 4. It will be appreciated that such double bonds provide opportunities for cis- trans isomeric forms. Two examples of alkenyl groups $R^1-CH=CH-$ are:

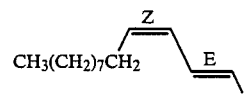

and

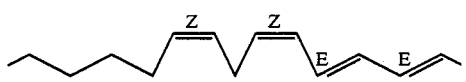

The group X is an alkylene radical having 1 to 6 carbon atoms. It can be branched or unbranched and is preferably unbranched, being of the formula —(CH$_2$)$_m$— where m is 1 to 6. X preferably contains 1 to 3 carbon atoms.

The group $R^2$ is preferably a carboxy group, —COOH, or a tetrazolyl group

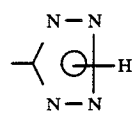

or either of these groups in protected form, preferably attached at the meta-position. The preferred compounds with optimum biological properties are the unprotected compounds but their protected forms may be required during the process of preparation. The substituent $R^2$ is most preferably tetrazolyl.

The value of $R^4$ in the nitrogen-containing Y group is hydrogen or $C_{1-4}$ alkyl such as, for example, methyl, ethyl, propyl, isopropyl and butyl. It is to be understood that in instances where there is more than one $R^4$ group attached to a moiety the values of the $R^4$ groups may be the same or different.

Carboxy-protecting groups are the well known ester forming groups used for the temporary protection of carboxylic acid groups. Examples of such groups which have general use are readily hydrolysable groups such as arylmethyl groups, haloalkyl groups, trialkylsilyl groups, alkyl groups, for example $C_{1-4}$ alkyl, and alkenyl groups. Other carboxy protecting groups are those described by E. Haslam in Protective Groups in Organic Chemistry, Chapter 5. It is usually necessary to protect any tetrazolyl group during the process of preparation, and suitable and well known protecting groups for this purpose include the trityl and benzhydryl groups, and optionally substituted benzyl for example p-methoxybenzyl, or a silyl group for example 5-butyl-diphenylsilyl. The preferred trityl protecting group can be readily formed by reaction with the appropriate halide in the presence of base for example by reacting the tetrazolyl reactant with trityl chloride and triethylamine. Such groups can readily be removed by acid treatment.

When the compound of formula (I) bears an unprotected carboxyl or tetrazolyl group, base addition salts can be prepared and these are to be regarded as part of the present invention. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms together with other pharmaceutically acceptable salts are particularly preferred.

The compounds of formula (I) also have a basic function by virtue of the nitrogen-containing group Y, and acid addition salts can be prepared. Examples of such salts are those derived from, preferably pharmaceutically acceptable, inorganic acids such as for example hydrochloric acid, phosphoric acid, sulphuric acid and nitric acid, as well as salts derived from strong organic acids.

It is to be understood that other non-pharmaceutical salts are included in the invention since they may be useful for identification, characterisation or purification of the free compound.

Compounds of formula (I) possess chiral centres at the carbon atoms bearing the hydroxyl and $SR^2$ groups and, accordingly, stereoisomeric forms exist R,R; S,S; S,R; R,S, the most preferred being 1S,2R. Other chiral centres are also possible, depending on the nature of the various substituents, which may lead to further stereoisomeric forms. Furthermore, the compounds exhibit cis-trans isomeric forms. All such stereoisomers, and racemic mixtures thereof, are included within the scope of the invention. Isomers can be isolated from racemic mixtures by conventional methods such as by the preparation of diastereoisomers with subsequent liberation of the enantiomers or, alternatively, can be prepared by methods devised to give the pure isomer.

A preferred group of compounds of the invention is one of formula (I) above in which Y has the value (i),

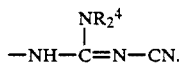

A further preferred group of compounds is one of the formula

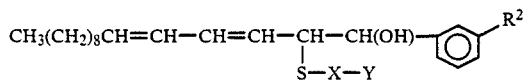

in which X, Y and $R^2$ have the values listed above for formula (I), and salts thereof. A particularly preferred group of compounds is one of formula (II) in which X is an alkylene group containing 1 to 3 carbon atoms, $R^2$ is tetrazolyl and Y is one of the values listed above for formula (I). The chiral configuration of carbon atoms 1 and 2 is preferably S,R, and the double bonds at carbon atoms 3 and 5 trans and cis respectively.

The invention also includes a process for producing a compound of formula (I) as defined above, which comprises reacting a compound of formula

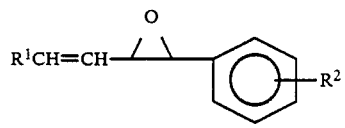 (III)

in which $R^1$ is as defined above and $R^2$ is —CN, —COOR$^3$ or

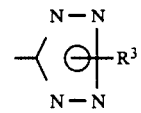

where $R^3$ is a protecting group, with a thiol of formula Y—X—SH, optionally followed by removal of a protecting group or by conversion of a nitrile group to tetrazolyl or carboxyl.

The reaction of compound of formula (III) with thiol is preferably carried out in an organic solvent such as an alcohol, for example methanol, in the presence of a base such as for example triethylamine and at a temperature of from 0° C. to 50° C.

It will be appreciated that it may be desired to remove any protecting groups attached to the product of the reaction. Such reactions can readily be carried out by use of a base in an inert organic solvent, such as for example, lithium hydroxide in tetrahydrofuran, or potassium carbonate in methanol, at a temperature of from 0° C. to 80° C., or by use of acid such as hydrochloric acid for removal of protecting groups from tetrazolyl by well known procedures described for example in the authorities referred to above.

Also it will be appreciated that an $R^2$ group when it is nitrile can be converted to tetrazolyl by reaction with, for example, sodium azide and ammonium chloride in dimethylformamide. Salts can be prepared from the tetrazolyl derivatives by the addition of base according to standard techniques. A nitrile compound can also be converted to a carboxyl derivative by treatment with base such as aqueous sodium hydroxide.

Compounds of formula (III) can be prepared by methods disclosed in European Patent Publication No. 0 134 111. For example, they may be prepared by the Wittig reaction of a phosphonium salt of formula $R^1CH_2P^+Ph_3Br^-$, in the presence of a base such as butyl lithium, with an aldehyde of formula (IV) or (V)

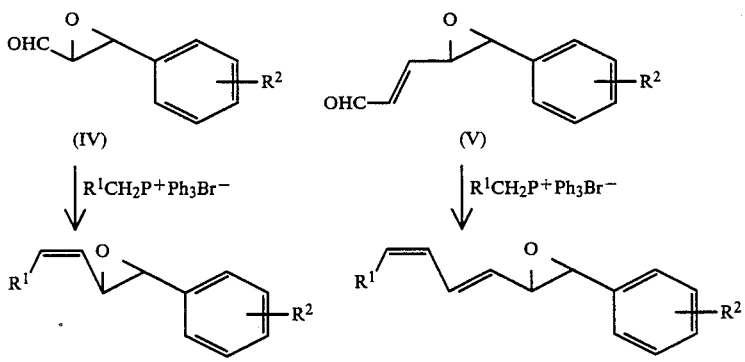

The reaction is generally carried out in an inert organic solvent such as for example, tetrahydrofuran, at a temperature of from −110° C. to 0° C.

Compounds of formula (IV) may be prepared from known intermediates by, for example, two principal routes. Firstly, they may be prepared, as racemic mixtures, by oxidation with, for example, hydrogen peroxide and sodium hydrogen carbonate in methanolic solution, of an aldehyde of the formula

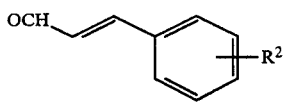

and, in its turn, aldehyde of formula (IV) may be converted to one of formula (V) by reaction with formylmethylenetriphenylphosphorane.

Alternatively, the compounds of formula (IV) may be prepared by oxidation of an epoxy alcohol of the formula

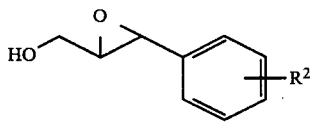

(VI)

with an oxidising agent such as, for example, chromium trioxide in pyridine. Compounds of formula (VI) can be prepared in stereospecific form and since the steric configuration is retained on oxidation to provide the aldehyde of formulae (IV) and, ultimately, of formula (V), this route can be employed to provide stereospecific compounds of formula (I).

Compounds of formula (VI) are prepared from the allyl alcohol

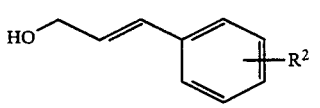

(VII)

using an epoxidising agent a reagent such as titanium isopropoxide and t-butyl hydroperoxide in the presence of L or D diethyl tartrate which yields the S,S or R,R epoxide with the above E olefin. When the Z olefin is used as starting material, the appropriate S,R and R,S stereoisomers result. Compounds of formula (VII) can be prepared from the appropriate benzaldehyde via a sequence of reactions involving reaction with malonic acid to provide the cinnamic acid derivative, treatment with oxalyl chloride to give the acid chloride, and reduction with a reagent such as lithium tri-t-butoxyaluminohydride or sodium borohydride.

The preparation of the thiol reactants of formula Y—X—SH is illustrated in the following Examples.

The compounds of the present invention are pharmacologically active, being leukotriene antagonists as shown by the in vitro test on guinea pig ileum segments at concentrations of from 10 ng to 50 μg, according to the method of Schild (1947) Brit. J. Pharm. 2, 197–206 (the unprotected compounds of formula (I) described in the following Examples exhibited as $IC_{50}$ against $LTD_4$ of less than $10^{-5}$ molar). Also compounds of the invention are active in the in vivo Guinea Pig Pulmonary Function Test of Austen and Drazen (1974) J. Clin. Invest. 53 1679-1685 at intravenous dosage levels of from 0.05 μg to 5.0 mg/kg and in a modified "Herxheimer" test (Journal of Physiology (London) 117, 251 (1952)) at doses of from 25 to 200 mg/kg. The "Herxheimer" test is based on an $LTD_4$- induced bronchospasm in guinea pigs which closely resembles an asthmatic attack in man.

The compounds are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever.

The compounds of the invention also have potential in the treatment of vascular diseases such as shock and ischaemic heart diseases for example coronary artery disease and myocardial infarction, cerebrovascular diseases, and renal diseases for example renal ischaemia.

Thus the invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for example by the oral or rectal route, topically or parenterally, for example by injection or infusion, and especially by inhalation, being usually employed in the form of a pharmaceutical composition. Such compositions are prepared in a manner well known in the pharmaceutical art and normally comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to product the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples. The structure of the compounds prepared was confirmed by I.R. and/or n.m.r. and/or mass spectra and the purity of the product was checked in most cases by HPLC. The involatile products were examined by mass spectrometry using the fast atom bombardment (FAB) technique in the negative ion mode. Significant [M—H]$^-$ ions (and characteristic fragment ions) were observed.

EXAMPLE 1

(R)-Methyl-N-acetyl-cysteine

A solution of N-acetyl-L-cysteine (3.26 g) (commercially available) in methanol (10 ml) with concentrated hydrochloric acid (four drops) was refluxed for 16 hours under a nitrogen atomosphere.

The methanol was evaporated in vacuo, and the residue partioned between saturated brine (2 ml) and dichloromethane (4×2 ml). The combined organic extracts were washed with water (2×8 ml), dried over magnesium sulphate and evaporated in vacuo to give the title compound as a nearly colourless oil, which crystallised on standing, m.p. 86°–87° C.

EXAMPLE 2

2-Carboxamido-2(R)-acetylamino-ethylthiol (R)-Methyl-N-acetyl-cysteine (1.20 g) was dissolved in a mixture of 0.880 ammonia solution (8 ml) and methanol (10 ml) and the clear solution stirred at room temperature under nitrogen for 48 hours.

The reaction mixture was evaporated firstly under a stream of nitrogen and then under high vacuum to give the product as a white gummy solid. Negative-ion DCI-MS (CH$_4$)m m/z 162, 161, 160, 129.

EXAMPLE 3

(1S,2R)-5-{3-[2-(2-Carboxyamido-2(R)-acetylamino-ethylthio)-1-hydroxypentadeca-3(E)-5(Z)-dienyl]-phenyl}-2-(triphenylmethyl)tetrazole To (1S,2S)-5-{3-[2-(1,2-oxido)pentadeca-3(E),5(Z)-dienyl]phenyl}-2-triphenylmethyl-2H-tetrazole (European Patent Publication No. 0 134 111) (300 mg) under nitrogen was added a mixture of 2-carboxamido-2(R)-acetylaminoethylthiol (from Example 2) (175 mg) and triethylamine (600 μl) in methanol (1 ml). The reaction mixture was stirred at room temperature under nitrogen for 60 hours.

The reaction mixture was blown down under nitrogen and the residue purified by column chromatography (silica; CH$_2$Cl$_2$ 10% MeOH) to give the product as a white foam, m.p. 75° C. (dec).

EXAMPLE 4

(1S,2R)-5-{3-[2-(2-Carboxamido-2(R)-acetylaminoe-thylthio)-1-hydroxypentadeca-3(E)-5-(Z)-dienyl]-phenyl}-1H-tetrazole A solution of (1S,2R)-5-{3-[2-(2-carboxamido-2(R)-acetylamino-ethylthio)-1-hydroxypentadeca-3(E)-5(Z)-dienyl]-phenyl}-2-(triphenylmethyl)-tetrazole (144 mg) in diethylether (2 mls), glacial acetic acid (1 ml) and water (1 ml) stirred at room temperature under nitrogen for 72 hours.

The ether was removed in vacuo, further water (4 mls) added, and the pH adjusted to 10 with solid sodium carbonate. The aqueous phase was washed twice with diethylether, acidified with 2 molar hydrochloric acid, and extracted five times with ethyl acetate. The combined ethyl acetate extracts were dried over magnesium sulphate and evaporated in vacuo to yield the title compound as a white solid, m.p. 98°–100° C.

EXAMPLE 5

(1S,2R)-5-{3-[2-(2-(N-Cyano-N'-methyl-guanidino)-ethylthio)-1-hydroxypentadeca-3(E),5(Z)-dienyl]-phenyl}-2-(triphenylmethyl)tetrazole To (1S,2S)-5-{3-[2-(1,2-oxido)pentadeca-3(E),5(Z)-dienyl]phenyl}-2-triphenylmethyl-2H-tetrazole (1.30 g) under nitrogen was added a mixture of N-cyano-N'-methyl-N"(2-mercaptoethyl)-guanidine (3.63 g of 16% w/v solution in methanol) (commercially available), methanol (2 ml) and triethylamine (2 ml). The clear reaction mixture was stirred at room temperature under nitrogen for 48 hours.

The reaction mixture was evaporated under a nitrogen stream and the residue purified by column chromatography (silica; eluant CH$_2$Cl$_2$ 10% methanol 1% acetic acid) to give the product as a yellow foam.

EXAMPLE 6

(1S,2R)-5-{3-[2-(2-(N-Cyano-N'-methyl-guanidino)-ethylthio)-1-hydroxypentadeca-3(E),5(Z)-dienyl]-phenyl}-1-H-tetrazole A solution of (1S,2R)-5-{3-[2-(2-(N-cyano-N'-methyl-guanidino)-ethylthio)-1-hydroxypentadeca-3(E)-5(Z)-dienyl]-phenyl}-2-(triphenylmethyl)-tetrazole (1.40 g) in a mixture of diethyl ether (20 ml), 98% formic acid (10 ml) and water (10 ml) was stirred at room temperature under nitrogen for 16 hours.

The ether was evaporated in vacuo, further water (10 mls) added, and the pH adjusted to 10 with solid sodium carbonate. The aqueous phase was washed twice with diethyl ether, acidified with 2 molar hydrochloric acid, and extracted five times with ethyl acetate. The combined ethyl acetate extracts were dried over magnesium sulphate and evaporated in vacuo to give a yellow foam (760 mg). The crude material was purified by column chromatography (Florisil; eluant (1) $CH_2Cl_2$ 1% acetic acid (2) $CH_2Cl_2$ 5% MeOH 1% acetic acid), to yield the title compound as a yellow foam, m.p. decomposes 160°–170° C.

EXAMPLE 7

(R,S)-Bis-(1-methyl-2,5-dioxo-4-imidazolidinyl-methyl)-disulphide

To a mixture of L-cystine (12 g) and 2 molar sodium hydroxide solution (50 ml), cooled to 0°–5° C. in an ice bath, was added, dropwise, methyl isocyanate (8.55 g). The clear solution was stirred at 0° for 2 hours, and then at room temperature over night.

The reaction mixture was cooled, washed with diethyl ether twice in a separating funnel, and acidified with concentrated hydrochloric acid (50 ml). After the addition of water (100 ml) the acidified reaction mixture was stirred at 100° C. for 2 hours.

The precipitated solid was collected by filtration, washed with ether on the sinter, and dried in vacuo to yield a white solid, m.p. ~260° C. (with decomposition).

EXAMPLE 8

1-Methyl-4-(R,S)-mercaptomethyl-2,5-dioxo-imidazole

To a solution of triphenylphosphine (3.3 g) in a mixture of dimethoxyethane (30 ml) and water (10 ml) was added bis-(1-methyl-2,5-dioxo-4-imidazolidinyl-methyl)-disulphide (from Example 7) (2.00 g). The reaction mixture was stirred over night at 50° C., under a nitrogen atmosphere.

The reaction mixture was evaporated in vacuo, the residual solid triturated with hexane, collected by filtration, washed with more hexane on the sinter and dried in vacuo to give the title compound as a white solid containing 40% molar triphenylphosphine oxide by NMR, m.p. 118°–120° C.

EXAMPLE 9

(1S,2R)-5-{3-[2-(1-Methyl-2,5-dioxoimidazolidin-4-(R,S)-yl-methylthio)-1-hydroxypentadeca-3(E)-5(Z)-dienyl]-phenyl}-2-triphenylmethyltetrazole Prepared by the method of Example 3 using 1-methyl-4-mercaptomethyl-2,5-dioxoimidazole (320 mg), (1S,2S)-5-{3-[2-(1,2-oxido)pentadeca-3(E),5(Z)-dienyl]-phenyl}-2-triphenylmethyl-2H-tetrazole (300 mg), triethylamine (400 μl) and methanol (2 ml).

The product after chromatography (silica:eluant 100% diethylether) was a white solid, softens 80° C.

EXAMPLE 10

(1S,2R)-5-{3-[2-(1-Methyl-2,5-dioxoimidazolidin-4-(R,S)-yl-methylthio)-1-hydroxypentadeca-3(E)-5-(Z)-dienyl]-phenyl}-1H-tetrazole Prepared by the method of Example 4 using (1S,2R)-5-{3-[2-(1-methyl-2,5-dioxoimidazolidin-4-(R,S)-yl-methylthio)-1-hydroxypentadeca-3(E),5-(Z)-dienyl]-phenyl}-2-triphenylmethyltetrazole (54 mg), 98% formic acid (1 ml), water (1 ml) and diethyl ether (2 ml).

The product was a white solid, m.p. 140° C.

EXAMPLE 11

2-(N-Ethylcarboxamido)-2(R)-acetylamino-ethylthiol

Prepared by the method of Example 2 using (R)-methyl-N-acetylcysteine (1.77 g) ethylamine (13 ml of 70% w/w aqueous solution) and methanol (20 ml), to give the title compound as a white solid, m.p. ~210° C. IR— NH 3280 $cm^{-1}$, amide C=O 1640 $cm^{-1}$.

EXAMPLE 12

(1S,2R)-5-{3-[2-(2-(N-Ethylcarboxamido)-2(R)-acetylaminoethylthio)-1-hydroxy-pentadeca-3(E)-5(Z)-dienyl]-phenyl}-2-triphenylmethyl-tetrazole Prepared by the method of Example 3 using 2-(N-ethylcarboxamido)-2(R)-acetylaminoethylthiol (380 mg), (1S,2S)-5-{3-[2-(1,2-oxido)pentadeca-3(E),5(Z)-dienyl]-phenyl}-2-triphenylmethyl-2H-tetrazole (608 mg), triethylamine (10 ml) and methanol (20 ml).

Chromatography (silica; eluant dichloromethane 5% methanol 0.1% acetic acid) gave the title compound as a yellow foam.

EXAMPLE 13

(1S,2R)-5-{3-[2-(2-(N-Ethylcarboxamido)-2(R)-acetylaminoethylthio)-1-hydroxy-pentadeca-3(E)-5(Z)-dienyl]-phenyl}-1H-tetrazole Prepared by the method of Example 4 using (1S,2R)-5-{3-[2-(2-(N-ethylcarboxamido)-2(R)-acetylaminoethylthio)-1-hydroxy-pentadeca-3(E)-5(Z)-dienyl]-phenyl}-2-triphenylmethyl-tetrazole (280 mg), glacial acetic acid (2 ml), water (2 ml) and diethyl ether (4 ml).

Reverse phase preparative HPLC (1" ODS TMS LP1 column;eluant 80% methanol 20% water 0.1% acetic acid) gave the title compound as a white solid.

$^1$H NMR: $CD_3OD$. 0.89δ t (3H), 1.09δ t (3H), 1.25δ m (14H), 1.94δ s (3H), 2.09δ q (2H), 2.68δ m (H), 2.82δ m (H), 3.18δ q (2H), 3.66δ m (H), 4.50δ m (H), 4.9δ d (H), 5.3–6.2δ m (4H), 7.6–8.05 m (4H).

EXAMPLE 14

2-(N-Butylcarboxamido)-2(R)-acetylaminoethylthiol

Prepared by the method of Example 2 using (R)-methyl-N-acetylcysteine (1.77 g), n-butylamine (14.60 g) and methanol (20 ml), to give the required product as a white solid.

EXAMPLE 15

(1S,2R)-5-{3-[2-(2-(N-Butylcarboxamido)-2(R)-acetylaminoethylthio)-1-hydroxy-pentadeca-3(E)-5(Z)-dienyl]-phenyl}-2-triphenylmethyltetrazole Prepared by the method of Example 3 using 2-(N-butylcarboxamido)-2(R)-acetylaminoethylthiol (436 mg), (1S,2S)-5-{3-[2-(1,2-oxido)pentadeca-3(E),5(Z)-dienyl]-phenyl}-2-triphenylmethyl-2H-tetrazole (608 mg), triethylamine (5 ml) and methanol (10 ml).

Chromatography (silica: eluant dichloromethane 5% methanol 0.1% acetic acid) gave the required product as a yellow wax.

EXAMPLE 16

(1S,2R)-5-{3-[2-(2(N-Butylcarboxamido)-2(R)-acetylaminoethylthio)-1-hydroxy-pentadeca-3(E)-5(Z)-dienyl]-phenyl}-1H-tetrazole Prepared by the method of Example 4 using (1S,2R)-5-{3-[2-(2-(N-butylcarboxamido)-2(R)-acetylaminoethylthio)-1-hydroxy-pentadeca-3(E)-5(Z)-dienyl]-phenyl}-2-triphenylmethyltetrazole (600 mg), glacial acetic acid (4 ml), water (4 ml) and diethyl ether (8 ml).

Preparative reverse phase HPLC (1" ODS TMS LP1 column; eluant 80% methanol 20% water 0.1% acetic acid) gave the title compound as a white solid.

$^1$H NMR: CD$_3$OD. 0.89$\delta$ t (6H), 1.15-1.55$\delta$ m (18H), 1.94$\delta$ s (3H), 2.08$\delta$ q (2H), 2.68$\delta$ m (H), 2.80$\delta$ m (H), 3.15$\delta$ t (2H), 3.68$\delta$ m (H), 4.45$\delta$ m (H), 4.9$\delta$ d (H), 5.3-6.4$\delta$ m (4H), 7.5-8.1$\delta$ m (4H).

The following formulations are given by way of example:

EXAMPLE 17

Soft Gelatin Capsule

Each soft gelatin capsule contains:

| Active ingredient | 150 mg |
| --- | --- |
| Arachis oil | 150 mg |

After mixing together, the blend is filled into soft gelatin capsules using the appropriate equipment.

EXAMPLE 18

Hard Gelatin Capsule

Each capsule contains

| Active ingredient | 50 mg |
| --- | --- |
| PEG 4000 | 250 mg |

The PEG 4000 is melted and mixed with the active ingredient. Whilst still molten the mixture is filled into capsule shells and allowed to cool.

EXAMPLE 19

Aerosol

| Active ingredient | 10 mg |
| --- | --- |
| Ethanol | 50 mg |
| Dichlorodifluoromethane (Propellant 12) | 658 mg |
| Dichlorotetrafluoroethane (Propellant 114) | 282 mg |

The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 or 100 μl equivalent to 0.5-1 mg active ingredient.

We claim:

1. A compound of the formula

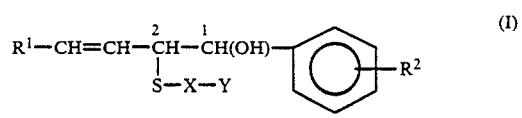

in which $R^1$ is $C_{7-20}$ alkyl, $C_{7-20}$ alkenyl or $C_{7-20}$ alkynyl, the alkyl, alkenyl or alkynyl group being optionally substituted by phenyl or phenyl substituted by 1 to 3 substituents selected from the group consisting of $C_{1-4}$ alkyl, $C_{1-4}$ alkoxy, hydroxy, nitro, cyano, halo, trifluoromethyl, carboxyl, tetrazolyl, and —CONH$_2$, $R^2$ is

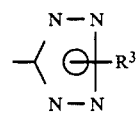

where $R^3$ is hydrogen, X is alkylene containing 1 to 6 carbon atoms and Y is a nitrogen-containing group selected from

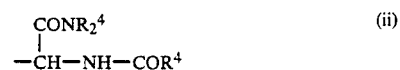

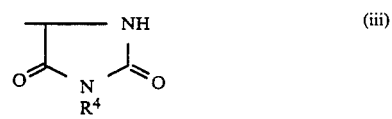

where each $R^4$ independently is hydrogen or $C_{1-4}$ alkyl; and pharmaceutically acceptable salts thereof.

2. A compound according to claim 1 in which $R^1$ is $C_{7-20}$ alkenyl and X is an alkylene group containing 1 to 3 carbon atoms.

3. A compound according to claim 1 in which $R^1$ is $R^5CH=CH$— where $R^5$ is $C_{7-11}$ alkyl or $CH_3(CH_2)_nCH=CH$—$CH_2$—$CH=CH$—$CH=CH$— where n is 0 to 4, and X is an alkylene group containing 1 to 3 carbon atoms.

4. A compound according to claim 3 in which Y is

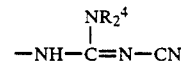

5. A compound of the formula

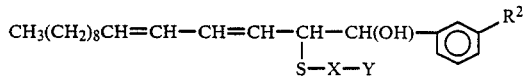

in which X is an alkylene group containing 1 to 3 carbon atoms, and Y is a nitrogen-containing group selected from

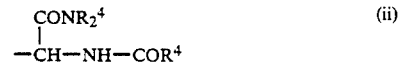

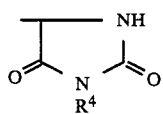 (iii)

where each $R^4$ independently is hydrogen or $C_{1-4}$ alkyl;

and pharmaceutically acceptable salts thereof.

6. A pharmaceutical formulation comprising a compound according to claim 1, and a pharmaceutically-acceptable diluent or carrier therefor.

7. (1S,2R)-5-{3-[2-(2-(N-Cyano-N'-methylguanidino)ethylthio)-1-hydroxypentadeca-3(E),5(Z)-dienyl]-phenyl}-1-H-tetrazole, and pharmaceutically acceptable salts thereof.

8. A method of treating a mammal, including a human, suffering from or susceptible to an allergic or vascular disorder which comprises administering an effective amount of a compound according to claim 1 or a pharmaceutically-acceptable salt thereof.

* * * * *